United States Patent
Gerder-Kallisch (10) Patent No.: US 9,788,801 B2
(45) Date of Patent: Oct. 17, 2017

(54) GAS ANALYZER, RESPIRATOR OR ANESTHESIA DEVICE WITH OPERATING GUIDE

(71) Applicant: Dräger Medical GmbH, Lübeck (DE)

(72) Inventor: Ulrike Gerder-Kallisch, Lübeck (DE)

(73) Assignee: DRÄGERWERK AG & CO. KGAA, Lübeck (DE)

(*) Notice: Subject to any disclaimer, the term of this patent is extended or adjusted under 35 U.S.C. 154(b) by 829 days.

(21) Appl. No.: 14/161,988

(22) Filed: Jan. 23, 2014

(65) Prior Publication Data

US 2014/0207015 A1 Jul. 24, 2014

(30) Foreign Application Priority Data

Jan. 24, 2013 (DE) .................. 10 2013 001 181

(51) Int. Cl.
- *G08B 5/00* (2006.01)
- *A61B 5/00* (2006.01)
- *A61B 5/08* (2006.01)
- *A61M 16/00* (2006.01)
- *A61M 16/01* (2006.01)
- *G06F 19/00* (2011.01)

(52) U.S. Cl.
CPC ............ *A61B 5/7475* (2013.01); *A61B 5/082* (2013.01); *A61B 5/742* (2013.01); *A61B 5/7405* (2013.01); *A61B 5/7435* (2013.01); *A61M 16/00* (2013.01); *A61M 16/0051* (2013.01); *A61M 16/0057* (2013.01); *A61M 16/01* (2013.01); *G06F 19/3406* (2013.01); *A61B 5/08* (2013.01); *A61M 2205/505* (2013.01); *A61M 2205/581* (2013.01); *A61M 2205/587* (2013.01)

(58) Field of Classification Search
CPC ....... A61B 5/7475; A61B 5/082; A61B 5/742; A61B 5/7405; A61B 5/055; A61B 5/14532; A61M 16/0051; A61M 16/01; A61M 16/0057; G06F 19/322; G06F 19/3412; G06F 19/3456
USPC .............. 340/815.4; 128/204.21, 203.14; 600/532, 431; 607/5, 32; 715/705, 772
See application file for complete search history.

(56) References Cited

U.S. PATENT DOCUMENTS

| | | | | |
|---|---|---|---|---|
| 2003/0208465 | A1* | 11/2003 | Yurko | G06F 19/322 |
| 2003/0216785 | A1* | 11/2003 | Edwards | A61N 1/3993 607/5 |
| 2004/0108995 | A1 | 6/2004 | Hoshino et al. | |

(Continued)

FOREIGN PATENT DOCUMENTS

| | | |
|---|---|---|
| DE | 10 2004 058264 B3 | 11/2005 |
| WO | 2009/063404 A1 | 5/2009 |

*Primary Examiner* — Hoi Lau (74) *Attorney, Agent, or Firm* — McGlew and Tuttle, P.C.

(57) ABSTRACT

A process for the control of a gas analyzer, respirator or anesthesia device (10), a control module (19) and a gas analyzer, respirator or anesthesia device (10) are provided with a control module (19). The process is used for the output of online help and for guiding the user via a sequence of operating steps that are executed via defined operational controls (17). Each operational control (17) is designed with a selection signal generator and with an activation signal sensor in order to make possible a visual selection of the respective operational control. The selection may be coupled with the output of a visual indication on the graphical user interface (13).

16 Claims, 3 Drawing Sheets

(56) References Cited

U.S. PATENT DOCUMENTS

| | | | |
|---|---|---|---|
| 2005/0010258 A1* | 1/2005 | Peterson | A61N 1/37247 607/32 |
| 2007/0245258 A1* | 10/2007 | Ginggen | A61M 5/14276 715/772 |
| 2008/0124692 A1* | 5/2008 | McEvoy | A61B 5/14532 434/262 |
| 2008/0133265 A1* | 6/2008 | Silkaitis | G06Q 50/00 705/2 |
| 2008/0279432 A1* | 11/2008 | Assmann | G06F 19/321 382/128 |
| 2009/0121592 A1 | 5/2009 | De Nando et al. | |
| 2009/0125757 A1* | 5/2009 | Knorl | A61B 5/055 714/47.1 |
| 2010/0199207 A1* | 8/2010 | Hopf | A61B 5/7475 715/772 |
| 2011/0251483 A1* | 10/2011 | Razzaque | A61B 6/466 600/424 |
| 2012/0017232 A1* | 1/2012 | Hoffberg | G06N 7/06 725/13 |
| 2012/0116196 A1* | 5/2012 | Tubb | G06F 19/3456 600/365 |
| 2012/0118292 A1* | 5/2012 | Aikawa | A61M 16/00 128/205.24 |
| 2012/0189173 A1* | 7/2012 | Markowitz | A61B 5/044 382/128 |
| 2013/0093829 A1* | 4/2013 | Rosenblatt | G09B 5/00 348/14.01 |
| 2014/0207015 A1* | 7/2014 | Gerder-Kallisch | A61B 5/7435 600/532 |
| 2014/0240349 A1* | 8/2014 | Tuukkanen | G06F 3/0484 345/633 |
| 2014/0311617 A1* | 10/2014 | Py | A61J 1/1406 141/1 |
| 2015/0169194 A1* | 6/2015 | Ban | D06F 39/005 715/771 |
| 2015/0286486 A1* | 10/2015 | Smith, III | G06F 9/4446 715/705 |
| 2016/0008083 A1* | 1/2016 | Kesten | A61B 5/062 600/424 |
| 2016/0210431 A1* | 7/2016 | Yu | H04L 67/10 |

* cited by examiner

GAS ANALYZER, RESPIRATOR OR ANESTHESIA DEVICE WITH OPERATING GUIDE

CROSS REFERENCE TO RELATED APPLICATIONS

This application claims the benefit of priority under 35 U.S.C. §119 of German Patent Application DE 10 2013 001 181.7 filed Jan. 24, 2013, the entire contents of which are incorporated herein by reference.

FIELD OF THE INVENTION

The present invention lies within the fields of electronics and medical engineering and pertains, in particular, to gas analyzers, respirators or anesthesia devices and the operation thereof.

BACKGROUND OF THE INVENTION

A gas analyzer, respirator or anesthesia device or other devices in the field of respiration technology and intensive medicine technology, as well as physiological monitoring usually comprise a plurality of functional components, such that the operation and control of the medical device is not a trivial task, especially since frequent, life-preserving procedures for the patient are connected with it. An anesthesia device or respirator, for example, is usually able to perform different device functions and therefore comprises an external data interface and different components, as well as a power supply and at least one control and regulation unit. In addition, the device consists of electrical and pneumatic components, such as actuators, which, e.g., can be designed for a respiration drive as a piston drive, blower drive or as a radial compressor. In an anesthesia device, a second actuator is usually provided as an anesthesia or medication dispensing means.

The usual, clinical operation and maintenance of the respective medical device requires a defined sequence of operating steps.

A problem in the previous devices according to the state of the art can be seen in that a user cannot possibly operate and/or control the device without error and appropriately when he does not have sufficient knowledge about the device and corresponding practical experiences in the operation of the device.

To support the user in this case in the operation or maintenance with further specific device information, it is known in the state of the art to provide a so-called online help as a special functionality. For this, a memory is designed in the device, in which the necessary device information is saved, e.g., in the form of electronic use, maintenance and/or operating guides, also comprising operating instructions. When a help symbol is activated on the user interface, the display of additional information on a graphical user interface is activated, as this is well known from computer technology in operating systems. The online help is particularly designed as context-sensitive, such that specifically only relevant information that is necessary for the respective operating situation is displayed.

An online help is known in the state of the art of printers or multifunctional devices. To support the user in defined device operations (e.g., removal of a paper jam), a corresponding message ("Open slot XY and then empty compartment AB") can be outputted (provided as an output) on a graphical user interface.

In complicated medical devices, it has proven to be a drawback in the state of the art that the user has to move through text information of the help menu, which is usually time-consuming. Another drawback of the above-mentioned prior-art process can be seen in that the user does not receive any information about the respective position or arrangement of the operational control to be operated at the device.

In order to support the user in the operation of an anesthesia device or respirator, it is also known in the state of the art to design an anesthesia device or respirator with a simulation functionality. Thus, DE 10 2004 058 264 B3 shows an anesthesia device or respirator with integrated simulation functionality to simulate device functions and to carry out suitable operating steps in a situation-related manner. The device reacts interactively to entries of the user. The properties of the device, for example, internal or external sensors and actuators are simulated here by means of simulation components and a simulation control.

SUMMARY OF THE INVENTION

Based on this state of the art, it is an object of the present invention to provide a gas analyzer, respirator or anesthesia device or another medical device with an improved user guide. It shall especially be possible to guide the user in the operation, testing, maintenance and/or cleaning of the device.

The object is accomplished by a control module, by a process, and by a medical device with such a control module.

Furthermore, the control module can be provided as a computer program or as a computer program product, such that the scope of protection of the present application also extends to the computer program product and the computer program.

The present invention makes possible an operating guide of the user, so that the user is directed by means of dynamically generated visual signals to the position of the respective operational controls to be operated at the device, so that an as efficient and error-free as possible operation of the device can be guaranteed. Via a provided simulation function, the user is supported in the operation of the device in a way that the user receives position data and further data for the operational controls of the device to be operated. Since respirators and anesthesia devices are used in life-threatening medical situations sometimes, a fast and efficient operation of the device via a sequence of operating steps which are to be executed individually in sequence is necessary. A fast and efficient operation of the device is supported by providing position data and other data on the operational controls provided by the present invention.

In order to operate, clean, perform maintenance on and/or disassemble and reassemble the respirator or other medical device, it is usually necessary to execute a specific sequence of operating steps. In a special embodiment, the present invention makes it possible for the user to be guided by this sequence of operating steps. In addition, the user preferably also receives indications about the position of the respective operational controls to be operated on the device without the user having to check the operating or maintenance guides, or without a simulation of the respective components being necessary. In the activation of a help function on the device, the present invention preferably makes it possible for the information necessary for operation as well as the operational controls of the device necessary for this being displayed to the user. The user is especially preferably signaled where the respective operational controls are precisely located at the device to guide the user through a chronology of device operating actions or a sequence of handling steps.

In one aspect, the present invention pertains to a process for the control of an anesthesia device or respirator or of another medical device that is operated, subjected to maintenance or tested with a sequence of operating steps, wherein at least some operating steps require actuation of operational controls, which are arranged at the medical device. The sequence of operational controls, which have to be operated for all operating steps, is automatically detected in the process.

The following process steps are iteratively executed for all or selected operational controls of the detected sequence of operational controls:
- sending at least one request signal to a selection signal generator of the respective operational control;
- outputting (providing an output of) at least one selection signal directly to the respective operational control (as a result, a selection functionality is provided);
- receiving at least one activation signal by an activation signal sensor, which is clearly associated with the respective operational control, in case the operational control has been operated correctly; and
- iteratively executing the send-output-receive steps for the respective next operational control of the detected sequence of operational controls.

Optionally, in addition, or as an alternative to outputting the selection signal to the respective operational control, a visual indication or an animated visual indication can be generated for the respective, next operational control to be operated and can be outputted on a graphical user interface. The visual indication can preferably comprise a direction indicator for position indication of the respective, next operational control to be operated and/or a context-sensitive help in case of incorrect operation of the operational control and/or in case no activation signal was received. The direction indicator in this case can preferably be in the form of an indicator arrow or in the form of an animated indicator arrow. An animated visual indication and an animated indicator arrow are defined in terms of the present invention as any form of a change in coloring, light intensity, size or shape, as well as also rhythmic or cyclical changes in the coloring, light intensity, size or shape of the visual indication or indicator arrow, for example, a blinking or a blinking sequence.

In an advantageous embodiment of the present invention, the process can be executed with access to a device memory, in which a device operating file is stored. The device operating file comprises a sequence of operating steps that must be executed for a defined operation of the device. In addition, an online help, which may have a hierarchical structure and provides additional information on different operational controls and/or topics, may also be filed in the device operating file.

The operation of the device may refer to a certain mode of operation or also be limited to specific operating forms (including maintenance, cleaning, normal operation, etc.). When requesting the help menu, the sequence of operating steps for the respective mode of operation is read out from the device memory and f process steps are iteratively executed for each individual operating step of the sequence of operating steps for the operation of the device.

The terminology used within the framework of this patent application is explained in detail below.

The medical device is preferably an anesthesia device or respirator. Alternative embodiments of the present invention pertain to gas meters or gas analyzers. Other alternative embodiments refer to devices in the clinical setting, which are preferably used within the framework of anesthesia and/or intensive care medicine and/or emergency medicine. The medical device comprises a graphical user interface. A plurality of operational controls is designed directly at the medical device for control or operation of the medical device. The operational controls may be designed as touch-, pull- or push-actuated switches, knobs, buttons, sliders, rotary knobs, as a special rotary knob, which may also be designed, for example, as a central actuating element (push-button), or even as an entry field on a user interface or on other I/O interfaces.

An operating step refers to an action that is to be performed at the medical device. An operating step may concern, for example, the entry of data, the operation of an operational control (button, switch, knob, etc.), the connecting of other components and/or, e.g., the reading in of data. An operating step may concern, for example, the setting of physiological parameters or the setting of respiration parameters. However, an operating step does not absolutely have to require the operation of an operational control. Thus, it is possible, for example, for certain control or operating steps to be automatically executed by the device (e.g., reading in of certain respiration parameters). It is also possible for an operating step to only require the operation of a single operational control (e.g., entry of a value on a touch screen surface). It may also be necessary that an operational control must be operated repeatedly for an operating step.

According to the present invention the operational controls of the device are expanded by additional components. An operational control thus preferably comprises:
- at least one selection signal generator, which is intended for outputting a selection signal to the respective operational control, and
- at least one activation signal sensor, which is intended for generating at least one activation signal in case of a correct operation of the operational control and sending it to the medical device, especially to a control module of the device.

The device memory is usually integrated directly into the medical device and comprises a device operating file, in which a sequence of operating steps and means for reading out the sequence of operating steps is stored. The device memory can be provided as the usual memory chip (e.g., as RAM, ROM, EEPROM, etc.). As an alternative, it is also possible to integrate the device memory not into the medical device, but rather to provide it as a separate memory entity, which is in data exchange with the medical device via corresponding interfaces. The "selection signal" is preferably a visual signal and is outputted directly to the respective operational control. It may be designed, for example, as a luminous or blinking LED. As an alternative, it is possible to provide an acoustic signal. Combinations of different types of signals are likewise conceivable. It is essential that the selection signal is outputted and provided directly at the operational control as a selection function.

The "activation signal" can be any electronic signal and be designed, for example, as a flag of a transmitted data set. It is preferably binary and thus identifies two statuses:
- an OK mode, which shall signal a correct operation of the respective operational control; and
- an error mode, which shall signal an incorrect or not-completed operation of the operational control.

The error mode may preferably be parameterized in a configuration phase. In this case, it is possible to set which statuses shall be covered by the error signal. Thus, it is, for example, possible to detect whether or if the respective operational control has been operated too late or not in the correct time interval. It is likewise possible to monitor whether the operational control has been operated at all. Alternative embodiments provide even further verification measures with regard to the respective operational control, which may also be represented via the activation signal. The activation signal is detected by an activation signal sensor, which is arranged directly at the operational control or is associated with same. The activation signal sensor may be, for example, position sensors, proximity sensors, temperature sensors, pneumatic sensors or any other sensors as well as also tactile elements or switching elements.

The operation of the gas analyzer, anesthesia device or respirator requires a sequence of operating steps which must be executed sequentially and/or partially in parallel (e.g., parallel operation of two operational controls at the same time). Usually a sequence of operational controls is to be operated for execution of each operating step. According to the present invention, provisions are now made for the user to be made aware at which position of the device the user has to operate which operational control before the user has to operate the respective operational control. For this, a request signal is sent to the operational control for each operational control to be operated, which leads to a selection signal being emitted to the operational control (e.g., the operational control lights up) and, in addition, the position is displayed via a corresponding visual indication with a direction indicator for position indication of the operational control to be operated on the graphical user interface. The visual indication preferably comprises arrows, which dynamically indicate the position of the respective operational control to be operated.

In the preferred embodiment the next operational control to be operated is identified by the selection signal and additionally by the visual indication. In a less complicated embodiment of the present invention, however, only one of the two identification variants (only selection signal or only visual indication on the user interface) may also be provided in this case.

In case the user has correctly operated the respective operational control over the course of time of the device operation, the process is executed iteratively for the next operational control, such that the user is directed to the next operational control to be operated. Here, the visual indication on the user interface is dynamically adapted to the respective operational control. Correspondingly, the selection signal generator of the next operational control is also activated. Thus, the user is guided by a sequence of operating steps to be executed.

The process is thus used for the displaying of information during the operation of the gas analyzer, respirator or anesthesia device on the graphical user interface. Here, an operational control, which is the next one to be operated, is additionally selected. As soon as the respective operational control has been operated correctly, an activation signal is detected at the operational control, which signals a correct operation and is preferably forwarded to a control module of the gas analyzer, respirator or anesthesia device. As soon as the activation signal has been detected, the process can be continued with the next operational control.

The visual indication which is displayed on the graphical user interface and the selection signal are thus outputted within a defined time sequence (and especially at the same time) and are dynamically adapted to the respective current operational control.

The control process according to the present invention advantageously takes into account a device operating status in a context-sensitive manner. Depending on the device operating status detected, certain excerpts of the device operating file are displayed on the graphical user interface and/or selection signal generators are activated or deactivated.

Provisions are usually made for the selection signal to then be outputted to the operational control, in case the operation of the respective operational control is immediately pending in order to direct the user to the operational control. In an advantageous variant of the present invention, provisions are made for the selection signal (possibly in changed form, e.g., the same light signal generator, but blinking) then to be outputted to the operational control as well, in case the respective operational control has been operated incorrectly or not at all. This is used to draw the user's attention to the fact that the user still has to make settings at the respective operational control. If required, an additional information box may appear on the graphical user interface to provide additional context-sensitive information as information text to the user. The selection signal is preferably outputted directly to the respective operational control. This has the essential advantage that the user has an additional position indication and is directed directly to the pending operation. Thus, the operation or control of the gas analyzer, respirator or anesthesia device can be carried out even more efficiently.

According to one aspect of the present invention, provisions are made for the selection signal to be executed on the operational control at the same time as or at least parallel to the displaying of the indication on the graphical user interface. Thus, the user can advantageously receive two different forms of indication for the pending operation.

According to an advantageous variant, provisions are made for all executed steps and especially all operations of the operational controls to be stored. This may be carried out in a log file in order to later have a basis for an error analysis or for training the user. In particular, all selection signals, request signals, activation signals and/or all other signals and/or output indications and messages are stored. The storage can be carried out in the device memory. The storage of the corresponding signals and operating steps can also be analyzed for statistical analyses and possibilities for device improvement.

In a preferred variant of the present invention, the device operating file is indexed and comprises a plurality of entry points for the selection of the sequence of operating steps. Thus, it is possible to execute the gas analyzer, respirator or anesthesia device also only for one operating excerpt or for certain functions, without it being necessary to operate the entire operation.

The device operating file containing the sequence of operating steps is preferably intended for the operation and/or maintenance of the gas analyzer, respirator or anesthesia device. In addition,—as already mentioned above—only individual excerpts of the device operation may be executed. Other alternative embodiments comprise the display of accompanying information and help information and other context-sensitive information, for example, for disassembling and for reconstructing individual device parts or of the entire device.

The embodiments of the process according to the present invention described above may also be embodied as a computer program product containing a computer program, wherein the computer is set to execute the process according to the present invention described above, when the computer program is executed on the computer or on a processor of the computer.

An alternative means of accomplishing the object also consists of a computer program containing a computer program code for executing all process steps of the process claimed or described above, when the computer program is executed on the computer. In this case, the computer program may also be stored on a machine-readable storage medium.

An alternative means of accomplishing the object provides a storage medium, which is intended for storing the above-described, computer-implemented process and is readable by a computer. It lies within the scope of the present invention that not all of the steps of the process have to be executed absolutely on one and the same computer entity, but rather they may also be executed on different computer entities. The sequence of the process steps may also be optionally varied.

In addition, it is possible that individual segments of the above-described process can be executed in one saleable unit (e.g., the operational control) and the remaining components in a different saleable unit (e.g., the control module or the device per se)—as a split system as it were.

The accomplishing of the object was described above in reference to the claimed process. Features, advantages or alternative embodiments mentioned herein are likewise also to be extrapolated to the other claimed subjects and vice versa. In other words, the objective claims (which, for example, are directed at a module or at a device) can be perfected with the features that are described or claimed in connection with the process. The corresponding functional features of the process are embodied here by corresponding objective modules, especially by hardware components, which, for example, can be implemented in the form of a microprocessor (µP), microcontroller) (µC), or in the form of instructions, which are filed in an electronic circuitry and are processed by a processor.

In one aspect, the control module comprises at least one interface for the graphical user interface, on which the visual indication with direction indicator shall be displayed and at least one interface for each one operational control of a plurality of operational controls, whereby one operational control is always embodied with a selection signal generator and with an activation signal sensor. Besides the interfaces, the control module comprises a device memory.

The control module is used for the guided and/or interactive execution of the sequence of operating steps of the gas analyzer, respiratory or anesthesia device. The control module can preferably be designed as a connectable support, help and/or guide module. The control module is preferably integrated directly into the gas analyzer, respirator or anesthesia device.

In an alternative, advantageous variant of the control module, the activation signal sensor can be designed not directly at the respective operational control, but rather at a different site of the gas analyzer, respirator or anesthesia device. Thus, it is possible also to detect still other activities that must be carried out at the device within the framework of the operation of the respective operational control. Basically, the activation signal which is detected by the activation signal sensor is used to display a correct operation of the respective operational control. "Correct operation" refers in this connection also to a correct chronological sequence of the operation. Thus, it is also possible to determine whether the correct operational control has been operated at the correct point in time. In an advantageous variant, the control module comprises a status detection unit or a status receiver, which is intended for continuously detecting a status of the gas analyzer, respirator or anesthesia device during the operation and outputs a context-sensitive message on the graphical user interface in case of an absent and/or incorrect operation of an operational control. The message may comprise an always dynamically generated visual indication, which comprises a direction indicator that refers to the operational control to be operated. Thus, the user's attention can advantageously be drawn to an absent or incorrect operation of an operational control. Optionally, it is also possible that, in addition to the message on the graphical user interface, another repeated selection signal is outputted on the operational control in order to be able to support the user even further.

Another aspect of the present invention refers to a medical device, in particular to a gas analyzer, respirator or anesthesia device that is designed with a control module described above. This device preferably comprises the graphical user interface, the different operational controls with selection signal generator and activation signal sensor and the control module.

In the detailed description of the figures below, exemplary embodiments, which are to be defined as nonlimiting, with their features and other advantages are discussed on the basis of the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Referring to the drawings in particular, the present invention is explained in detail below with reference to FIG. 1.

Figure 1:
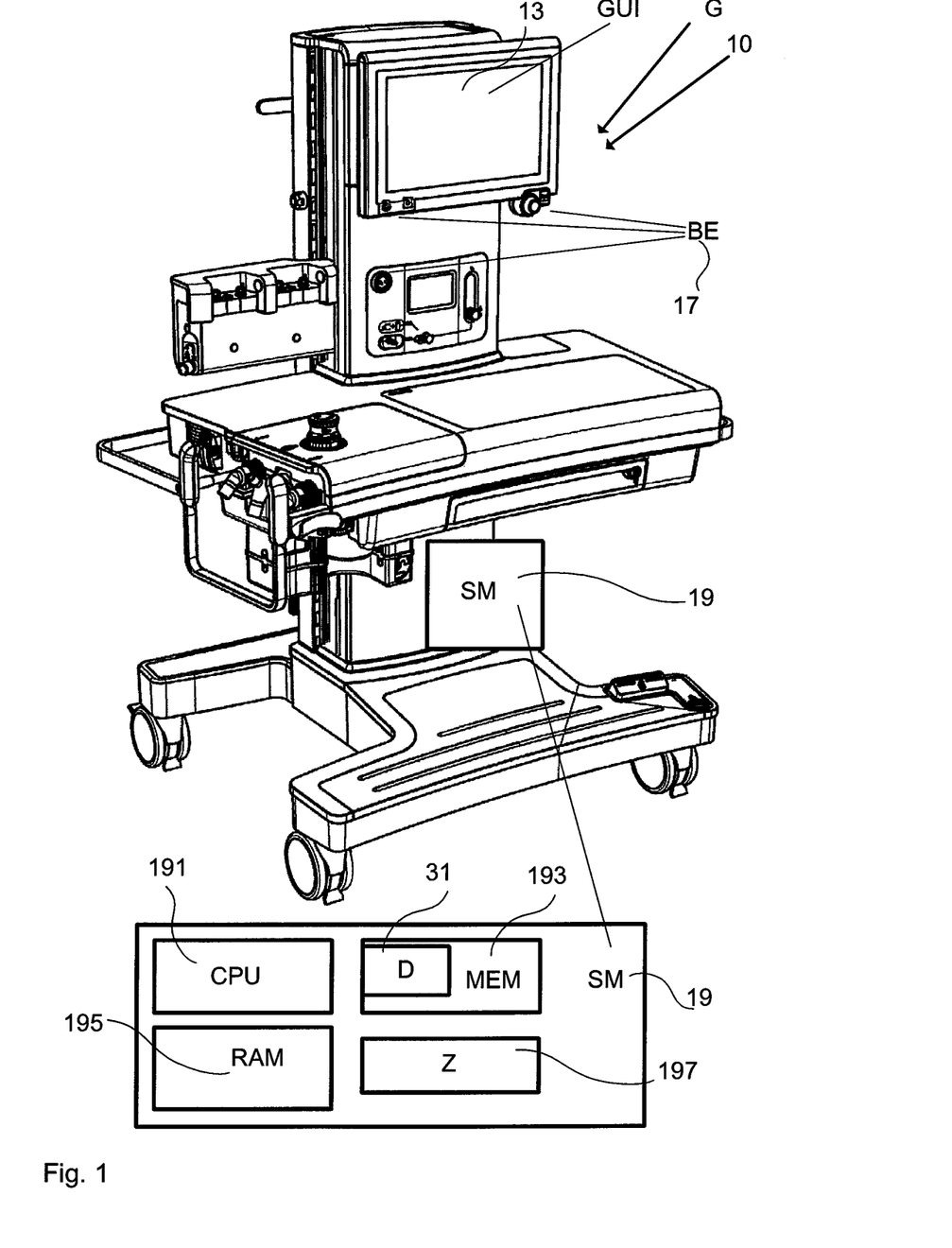
FIG. 1 is a schematic view of a gas analyzer, respirator or anesthesia device, with a control module according to a preferred embodiment of the present invention.

The present invention pertains to a possibility for controlling a gas analyzer, respirator or anesthesia device, whereby an anesthesia device as device G, 10 is shown as an example in this FIG. 1. The present invention may, however, be pertinent not only to gas analyzers, respirators or anesthesia devices, but also to emergency respirators, lung monitoring systems, drug measuring devices, gas measuring systems or other medical devices, which have a graphical user interface GUI, 13 and operational controls BE, 17. A sequence of operating steps BS, 11 (FIG. 2) is usually executed on the medical device. The present invention is used for a guided or interactive execution of the required sequence of operating steps BS, 11 (FIG. 2), whereby the user shall be guided from step to step. In this case, usually always one operating step requires at least partially an actuation of operational controls BE, 17. An operational control BE, 17 can be, for example, an adjusting element, a switch, a potentiometer, data on a user interface or a push-button or rotary knob.

To which functions the respective operating steps are pertinent in terms of content is of secondary importance for the implementation of the present invention. Thus, the operating steps may, on the one hand, be dedicated to the normal operation, e.g., of the device G, 10; however, it is also possible that the operating steps BS, 11 (FIG. 2) are used for maintenance or for correcting an error.

Since the user shall now be guided by the operational controls BE, 17 to be actuated in succession, provisions are made according to the present invention to inform the user about the type and position of the respective, next operational control BE, 17 to be operated. For this, each operational control BE, 17 is designed with a selection signal generator MSG, 33 (FIG. 2) and an activation signal sensor ASG, 29 each (FIG. 2).

In a less complicated embodiment, only selected and relevant operational controls BE, 17 are equipped with selection signal generator MSG, 33 (FIG. 2) and/or activation signal sensor ASG, 29 (FIG. 2) (for example, those operational controls BE, 17 which must be operated in practice frequently or in clinical use).

Figure 2:
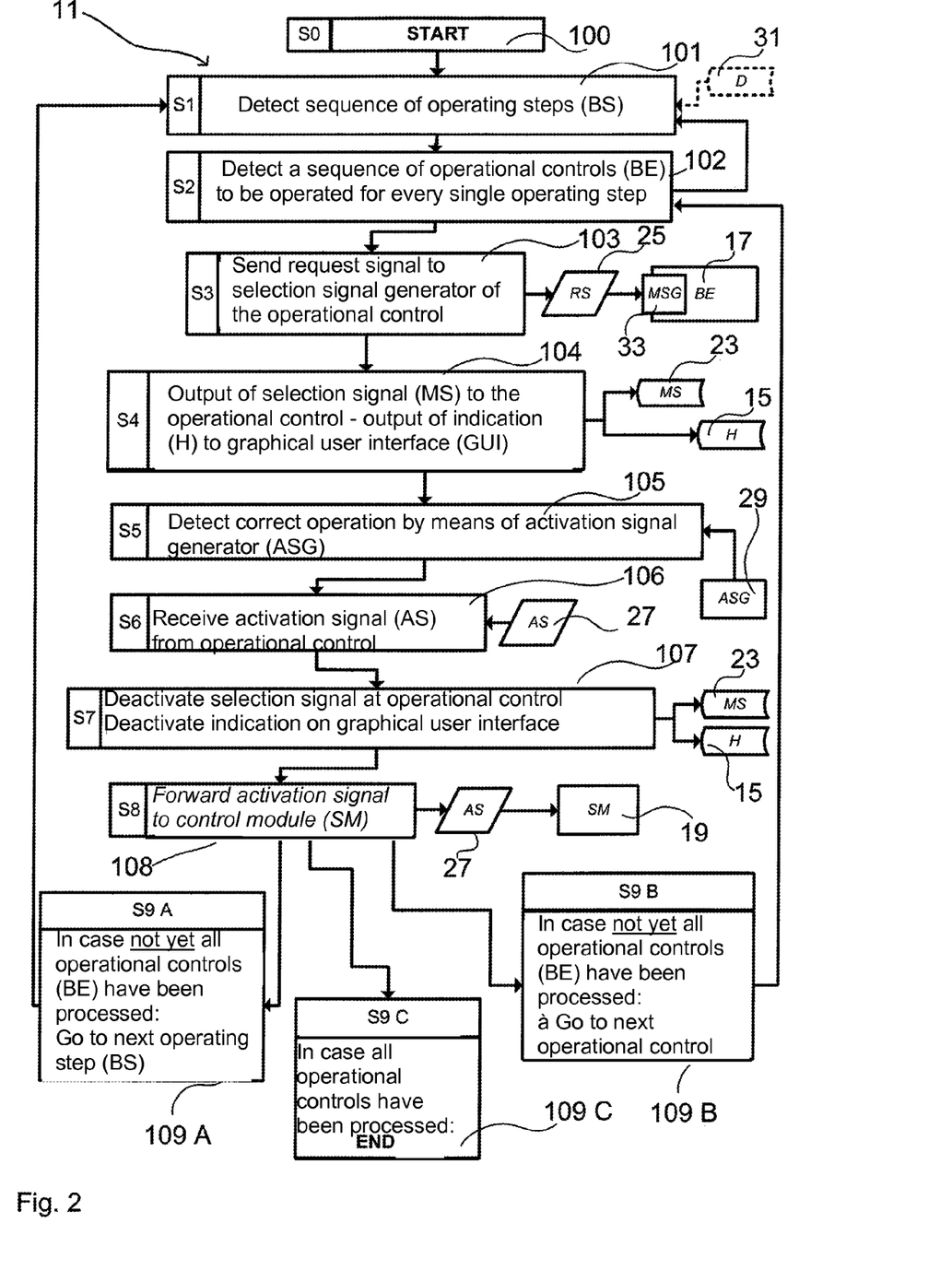
FIG. 2 is a flow chart for a process for the control of a gas analyzer, respirator or anesthesia device according to the present invention.

The selection signal generator MSG, 33 (FIG. 2) is intended for receiving a request signal RS, 25 (FIG. 2) from the control module SM, 19 and consequently for activating the selection signal generator MSG, 33 (FIG. 2). Preferably, it is possible to determine in a configuration phase which selection signal MS, 23 (FIG. 2) the selection signal generator MSG, 33 (FIG. 2) shall output. Preferably, a visual signal is provided in this case, such that the selection signal generator MSG, 33 (FIG. 2) of the respective operational control BE, 17 preferably blinks (for example, by means of an LED or by other lighting bodies) or is continuously brightly lit. As an alternative or cumulatively, an acoustic or other signal may also be outputted in this case. It is essential that the selection signal MS, 23 (FIG. 2) is outputted immediately and directly to the respective operational control BE, 17 to draw the user's attention to the respective operational control and the position thereof. Since some of the operational controls BE, 17 are also located on the reverse side of the device G, 10, this may be helpful additional information for the user.

The activation signal sensor ASG, 29 (FIG. 2) is preferably arranged at the respective operational control BE, 17 as well and is used to detect a correct operation of the respective operational control BE, 17. The activation signal sensor ASG, 29 (FIG. 2) can preferably be designed as a pressure sensor, as a tactile sensor or the like in order to detect a user interaction. For example, the operation of a switch or of another tactile element can be detected in this case. If the activation signal sensor ASG, 29 (FIG. 2) generates an activation signal AS, 27 (FIG. 2), the activation signal AS, 27 (FIG. 2) represents that the respective operational control has been operated correctly. "Correct operation" means in this connection a correct functional operation and also a correct operation at a correct point in time. The activation signal AS, 27 (FIG. 2) is sent to the control module SM, 19 (FIG. 2) for further processing. The control module SM, 19 (FIG. 2) comprises at least one input/output interface to the graphical user interface GUI, 13 and a device memory MEM, 193 that is designed for storing a device operating file D, 31.

As mentioned above, the present invention is used for supporting the user in a multistep operating process, in which a plurality of operational controls must be operated in succession. For this, the present invention has basically two measures:

outputting a selection signal MS, 23 (FIG. 2) to the respective operational control BE, 17; and
outputting a visual indication H, 15 (FIG. 2) on the graphical user interface GUI, 13.

The visual indication H, 15 (FIG. 2) comprises a direction indicator, which displays the respective position of the next operational control BE, 17 to be operated.

Figure 3:
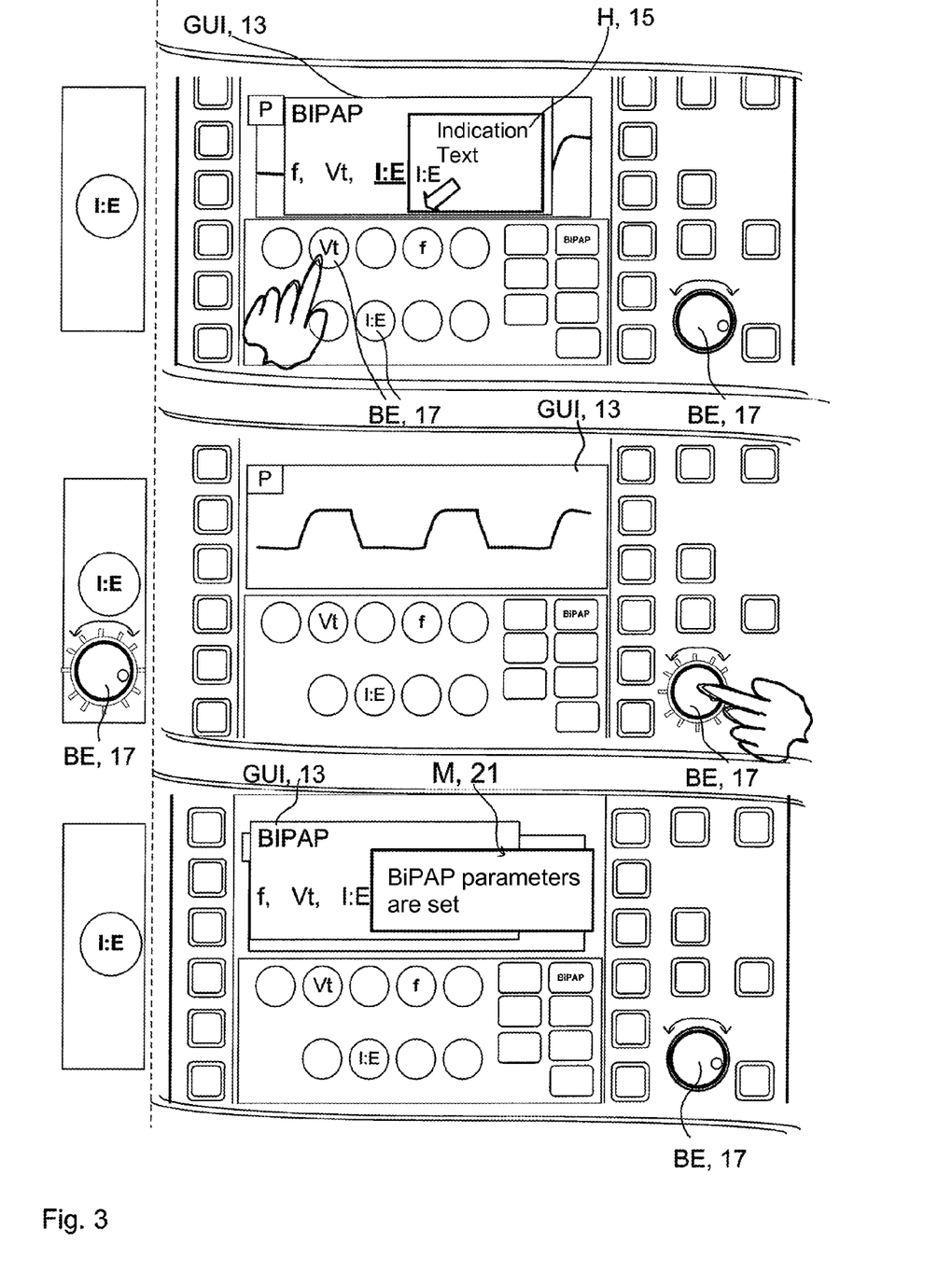
FIG. 3 is a schematic view of a visual indication on a graphical user interface and operational controls of a medical device, which are each designed with a selection signal generator.

Visual indication H, 15 (FIG. 2) can be designed here as an independent element on the graphical user interface GUI, 13, but visual indication H, 15 (FIG. 2) can preferably be designed as at least one partial element of a message M, 21 (FIG. 3). The direction indicator is preferably dynamically updated and always refers to the respective, next operational control BE, 17 to be operated. The direction indicator is preferably designed, such that the position of the next operational control BE, 17 to be operated relative to the position of the indication H, 15 (FIG. 2) proper is displayed. For example, the direction indicator can be shown in the form of an arrow on the graphical interface GUI, 13, whereby the arrow H, 15 (FIG. 2) refers in direction to the operational control BE, 17 to be operated.

In case the operational control BE, 17 is also located on a reverse side of the respirator, then the user is referred to the respective position of the operational control BE, 17 by a corresponding arrow setting, which refers to the reverse side of the device G, 10. As an alternative, a plurality of arrows may also be visualized, whereby one arrow is lit more brightly sequentially in each case to identify a position by the chronological sequence of the changing lighting.

According to an advantageous variant, the present invention comprises, besides the two above-mentioned possibilities, another further option for supporting the user, in particular:

outputting the message M, 21 (FIG. 3) on the graphical user interface GUI, 13.

The message M, 21 (FIG. 3) is preferably provided in a text format and can comprise an excerpt from a device operating file D, 31. Here, the user can be informed, for example, about the next action to be executed in each case and additional accompanying information and this can take place, for example, in case of problems with a noninvasive blood pressure (NBP) measurement in the following information text:

"NBP blood pressure cuff defect or NBP hose jammed."

In noninvasive blood pressure measurement, a systolic pressure and a diastolic pressure of the blood in the bloodstream of the patient are measured by means of applying an external pressure by means of a cuff inflatable with air, for example, on the upper arm of a patient. The pressure measurement in this case may be misrepresented or may not able to be carried out due to an incorrect operation. In such situations, additional accompanying information represents a helpful support for the user. The user can, in addition, be further supported by further messages M, 21 (FIG. 3) being initiated, which, for example, indicate connection possibilities for various additional modules, which can be located, for example, on a side front or on the reverse side of the device G, 10. Thus, for example, a slot compartment on the reverse is provided on a product (Dräger Infinity Delta XL) of the Applicant, on a physiological monitor, for the connection of additional modules. For example, a module for measuring a gas concentration, for example, a carbon dioxide concentration ($CO_2$), in particular a measurement of an end-tidal carbon dioxide concentration ($etCO_2$) can be inserted into this slot compartment. An end-tidal carbon dioxide concentration (etCO$_2$) is defined as a carbon dioxide concentration at the end of the expiration phase of the patient, before the inspiration begins.

The control module SM, 19 has (bidirectional) interfaces to the respective operational controls (at least to those that are equipped with a selection signal generator MSG, 33 (FIG. 2)) and to the device memory MEM, 193 and to the graphical user interface GUI, 13.

The structure of the control module SM, 19 according to a preferred embodiment of the present invention is schematically explained in detail in FIG. 1. Control module SM, 19 in this case comprises a processor unit CPU, 191, the device memory MEM, 193 with the possibility for storing a device operating file D, 31, an additional memory RAM, 195, for example, a working memory and a status detection unit Z, 197. The status detection unit Z, 197 is, however, only optional and is used to continuously detect a device status of the device G, 10 during the operation of the device. In case an absent and/or incorrect operation of an operational control BE, 17 was detected, a context-sensitive message M, 21 (FIG. 3) and/or the dynamically generated visual indication H, 15 (FIG. 2) with the dynamically adapted direction indicator is automatically outputted on graphical user interface GUI 13 to direct the user to the next actions. In alternative embodiments, the control module SM, 19 may, however, comprise even further modules, for example, an acoustic module in order to output spoken messages over the loudspeaker system.

The control module SM, 19 is preferably integrated into the device G, 10. As an alternative, control module SM, 19 may, however, also be provided as a separate module, which can be connected to the device G, 10 via corresponding interfaces (for example, wireless, such as Bluetooth, etc.).

An operating sequence beginning with a "START" S0 100, divided into a sequence of nine steps S1 101 through S9 109 of a control process for a device G, 10 (FIG. 1) is described below in detail with reference to FIG. 2. Device G 10 (FIG. 1) is, for example, called a medical device in this FIG. 2, and in particular, a gas analyzer, respirator or anesthesia device. In addition, other medical devices with a graphical user interface GUI, 13 (FIG. 1, FIG. 3) and operational controls BE, 17 (FIG. 1, FIG. 2, FIG. 3) and also emergency respirators, lung monitoring systems, drug measuring devices, gas measuring systems are also included within the scope of the present invention.

After the start S0 100 of the process, a sequence of operating steps BS, 11 is detected, for example, from the device operating file D, 31 in step 1 S1 101: Detect sequence of operating steps (BS).

In step 2 S2 102 Detect a sequence of operational controls (BE) to be operated for every single operating step (BS), a sequence of operational controls BE, 17 to be operated is detected for every single operating step BS, 11. Steps 1 and 2 may also be executed nested in one another.

In step 3 S3 103 Send request signal (RS) to selection signal generator (MSG) of the operational control (BE), a request signal RS, 25 is sent to the respective selection signal generator MSG, 33 of the respective operational control BE, 17. Request signal RS, 25 is used to activate the selection signal generator MSG, 33 on the respective operational control BE, 17. If a plurality of selection signal generators MSG, 33 are provided on an operational control BE, 17, the request signal RS, 25 may be specified correspondingly.

Consequently, in step 4 S4 104 Output of selection signal (MS) to the operational control (BE), output of indication (H) to graphical user interface (GUI), selection signal MS, 23 is outputted to the operational control (e.g., by one or more constantly or intermittently luminous LEDs).

In step 5 S5 105 Detect correct operation by means of activation signal generator (ASG), a correct operation is then detected by the activation signal generator ASG, 29. In this case, it is particularly determined whether the user operated the respective operational control BE, 17 at the correct point in time in the correct manner.

In step 6 S6 106 Receive activation signal (AS) from operational control (BE), an activation signal AS, 27 is sent from the respective operational control BE, 17 to the control module SM, 19 if the user operated the respective operational control BE, 17 at the correct point in time in the correct manner (step 5 S5, 105).

In step 7 S7 107 Deactivate selection signal at operational control (BE) Deactivate indication (H) on graphical user interface (GUI), deactivation of the selection signal MS, 23 and of the indication H, 15 takes place on graphical user interface GUI, 13, since these selections are no longer necessary, since the respective operational control has been operated correctly.

In step 8 S8 108 Forward activation signal (AS) to control module (SM), the activation signal AS, 27 is consequently forwarded to the control module SM, 19 for further processing.

After step 8 S8 108, a case distinction is made in step 9 into three cases: S9 A 109A; S9B 109B; S9C 109C.

S9 A 109A: In case not yet all operational controls (BE) have been processed:→ Go to next operating step (BS), if all operational controls BE, 17 have been processed, a jump is made to the respective, next operating step BS, 11 and the process can be continued at step 1 101 with the next operating step BS, 11. This is shown in FIG. 2 on the left side with a reference/return to step 1.

S9 C 109C: In case all operational controls have been processed: END, if all operational controls BE, 17 of all operating steps BS, 11 have been processed, the process can be ended or be iteratively repeated for another process (e.g., maintenance). This is shown in FIG. 2 in the middle.

S9 B 109B: In case not yet all operational controls (BE) have been processed: → Go to next operational control (BE), if not yet all operational controls BE, 17 have been processed, a jump is made to the respective next operational control BE, 17. This is shown in FIG. 2 on the right side, with a reference/return to step 2.

Steps 3 S3 103 through 8 S8 108 are then executed for the respective, next operational control BE, 17.

The repetition of steps 2 S2 through 8 S8 is carried out for all operational controls BE, 17 that are necessary for the control of an operating step BS, 11. Steps 2 through 8 are thus executed iteratively for all operational controls BE, 17.

Further advantageous variants of the present invention are explained in detail below with reference to FIGS. 1, 2, 3.

In an advantageous variant of the present invention, provisions are made that the visual indication H, 15 to be displayed on the user interface GUI, 13 is additionally coupled with further information. For example, a linking can be provided via a central device control of the device G, 10 or additional subfunctions of the device control (comprising display routines, screen control, detection routines, event detection, sequential control, etc.). Thus, it is possible to provide, as it were, an electronic use guide or relevant excerpts thereof directly on the device G, 10, which is shown on the screen GUI, 13. For example, a window can be displayed for this. The window can overlay the usual operating window or be shown on an additional screen, for instance, if a multi-monitor configuration with a plurality of screens is selected. It is also possible to display visual indication H, 15, a message M, 21 and/or other additional information on a separate screen. This may be, for example, an external device, e.g., a laptop computer, a netbook computer, a Smartphone or a tablet PC. These external devices are connected to the control module SM, 19 via a corresponding (wireless) interface. In case, for example, an operating step BS, 11 provides the connection of a breathing tube on the front side on the anesthesia device, then the user can be informed, by means of an indicator arrow, which can be coupled with the indication text, on the display about the action to be carried out. In addition, the device port for the expiratory tube port can be designed with selection signal generator MSG, 23, whereby the selection signal generator MSG, 33 lights up. The user then knows, at which of the two (inspiratory/expiratory) tube ports the user must connect the respective tube.

If the respective operational control BE, 17 is not located on the front side of the device G, 10, but rather, for example, on the side or on the reverse side (e.g., gas port or electrical port), then according to the present invention, at least one animated indicator arrow H, 15 (two-dimensional or three-dimensional arrows, which point to the spatial position at the device) is outputted. If, for example, an action shall be executed at the NBP port, which is located on the side of the device (e.g., at a physiological monitor of the Applicant: Dräger Infinity Delta XL), then the user is referred by corresponding animation to the reverse side (for example, in the form of an arrow chain with running light effect with direction from bottom left to middle right).

Another exemplary embodiment refers to an indicator arrow H, 15 on the display GUI, 13 for the identification of the port for a sampling tube on a breathing gas analyzer or breathing gas meter (oxy-capnometer or breath-alcohol meter).

Another application possibility of the control process according to the present invention for carrying out defined operating steps BS, 11 can also be used for cleaning the device G, 10. If, for example, the cover plate of a respirator is to be cleaned, then the user can be informed via corresponding indicator arrows H, 15 that the cleaning of the cover plate shall be done by means of a wiping disinfection. Some devices of the Applicant may be mentioned as respirators, e.g., Dräger EVITA XL, Dräger EVITA 4, Dräger CARINA, Dräger EVITA Infinity V500. A device of the Applicant may be mentioned as a physiological monitoring device, e.g., Dräger Infinity Delta XL. Devices of the Applicant may be mentioned as anesthesia devices, e.g., Dräger PRIMUS, Dräger ZEUS, Dräger PERSEUS A500. The indication arrows H, 15 can, for example, "select" the cover plate of the device G, 10 in the form of a running light with sequentially blinking arrows from left to right on the top side of the operating and output screen GUI, 13.

Another application possibility refers to the maintenance of the device G, 10. In this case indicator arrows can be used to remove this cover plate in the course of the maintenance Examples of such maintenance procedures are, e.g.:
electrode cable wiping disinfection
empty water trap
replace $O_2$ sensor
replace flow sensor, etc.

Here, indicator arrows H, 15 can refer to the fastening elements (e.g., screws) on the device G, 10, which must be loosened for the maintenance procedure. In case, for example, the cover plate is to be removed, a corresponding message "remove cover" could be identified by cyclically descending or rising arrows. An additional identification can take place on the interface GUI, 13 by a symbolic display being executed, which shows the respective operational control (e.g., flow sensor) to direct the user to the respective replacement part. This embodiment is therefore advantageous, since the message M, 21 contains not only text information, but, as an alternative or in addition, another symbol display of the respective operational control BE, 17.

This has the advantage that translation into other languages is not necessary. Basically, the type of selection signal MS, 23 is not limited to a defined form and can comprise a constant lighting, a rhythmic-blinking lighting or even other types of signals (e.g., acoustic). The type of operational control BE, 17 (e.g., adjusting elements, switches, etc.) is also not limited and can hence also be used for input fields on a graphical user interface GUI, 13.

It is also possible to provide a plurality of selection signal generators MSG, 33 on an operational control BE, 17, which differ, for example, in their color, such that, for example, one red and one green LED can be provided. The two selection signal generators then signal each different operating states of the operational control BE, 17. Accordingly, for example, the green LED may concern a correct operating state of the operational control BE, 17 (e.g., of a plug, of an $SPO_2$ sensor on the front side of a physiological monitor). The selection signal generator MSG, 33 can thus be designed as a status indicator, such that a green LED indicates a correct electrical plug-in connection between the $SPO_2$ sensor and monitor, while the red LED signals an incorrect plug-in connection. Another functionality can be provided on the selection signal generator MSG, 33 by a selection signal generation being configured in a preparation phase. Thus, it is, for example, adjustable that a green-blinking selection signal generator MSG, 33 leads or guides the user in combination with an indication text H, 15 on the interface GUI, 13 to the respective connection to be operated.

As was already explained above, it is possible that the respective operational control BE, 17 is not a mechanical or electromechanical switch or button, but rather an input field or another control panel on the graphical user interface GUI, 13, which, for example, is shown on a touch-sensitive display. The operational control BE, 17 is thus a button on the graphical user interface GUI, 13. It is possible here that the respective operational control BE, 17 is symbolically and graphically simulated as a virtual operational control, as it were, and is shown on the user interface. This may be, for example, the symbolic display of a virtual adjusting knob for a respiration parameter (e.g., respiration rate f, an inspiration time T1 or an inspiration-expiration ratio I:E ratio or tidal volume $V_T$). The selection signal generator MSG, 33 is then designed as a selection element on the graphical user interface GUI, 13. The selection signal generator MSG, 33 can be designed as a visual highlighting by color change, a blinking, a change in brightness and/or contrast/or a local increase in brightness at the operational control BE, 17 against the background in the respective screen region on the interface.

Preferably, the control process is divided into two types:
a preparation or configuration phase; and
an operating phase.

In the configuration phase, a configuration menu is usually displayed on an interface in order to find and to define different settings of the control process. For example, it is possible in this case to configure how the visual indication H, 15 and/or context-sensitive message M, 21 (FIG. 3) shall appear on the interface GUI, 13. For example, the two elements (indication H, 15 and message M, 21 (FIG. 3)) can be arranged in a separate window, which shall be located at a defined site on the interface GUI, 13. Furthermore, the entire device operating file D, 31 or an excerpt thereof can be displayed in order to provide additional information to the user. The selection in this case is likewise configurable. It is also possible to configure how the popup window shall be displayed. For example, it can always be displayed in the foreground (in relation to the Z axis always at the so-called "topmost position" or in the background, in case the window should not appear in focus, provide with a background color, formattings for the characters can be selected, the window can overlay or be displayed transparently or partially transparently). It is also possible to configure the display duration. It is essential that the appearing popup window indeed be adapted to the configuration wishes of the user, but that essential device control functions are not covered, and thus it is guaranteed that essential device functions remain operatable, even when the popup window is displayed.

A display possibility for the device operating file D, 31 is explained in detail below on the basis of an exemplary embodiment of the present invention. In this case, the device operating file D, 31 comprises different levels of hierarchy for the referenced documents. Thus, for example, the following five-stage document hierarchy (depending on the complexity of the respective device G, 10) can be provided:

First level: Online help (example: Control)
Second level: Chapter headings (example: forms of respiration)
Third level: Main headings (example: BiPAP; Biphasic Positive Airway Pressure)
Fourth level: Subheadings (example: Respiration parameters)
Fifth level: Operational control 1 (example: Respiration rate f),
Operational control 2 (example: Tidal volume VT),
Operational control 3 (example: I:E ratio)

In an advantageous variant of the present invention, provisions are made for the user to be able to select a specific help topic from the range of topics. For this, for example, the device operating file D, 31 may contain defined topics in different levels of hierarchy (as already described above by way of example). Thus, it is, for example, possible, to select the help topic BiPAP (BiPAP guide). If the user has selected a specific help topic from the graphical user interface GUI, 13, a hyperlink may be started from the online help. In addition, it is possible to guide the user in a guide mode by means of defined steps of the device control. For this, a defined sequence of operating steps is determined: $BS_1$, $BS_2$, ... $BS_n$, which are each processed sequentially. In more complicated embodiments, it is also possible to execute all or selected operating steps BS, 11 in parallel. In this case, an operating step BS, 11 may require the operation of the operational control BE, 17. Of course, it is also possible that an operating step BS, 11 requires the operation of a plurality of operational controls BE, 17. For this, an indication text may in each case be outputted on the graphical user interface GUI, 13, which refers to the operation of the respective operational control. In addition and optionally, it is possible to select the respective operational control BE, 17 by means of the selection signal generator MSG, 33. The operation of the user is detected via the activation signal sensor ASG, 29. This may be, for example, a so-called smart key control or the pushing/turning of the central rotary knob or any other operational controls BE, 17. After all operational controls BE, 17 and all operating steps BS, 11 have been executed, the guide mode for the respective help topic ends, and a corresponding indication text may optionally be outputted for ending the guide mode. Consequently, the device operation can be continued normally.

An exemplary embodiment for a process for control of the device G, 10 in guide mode is described in detail below. The user selects "respiration parameters" in the online search. Consequently, the associated operational controls BE, 17 are selected at the device G, 10 by the visual selection signal generator MSG, 33. In addition, a corresponding indication text is optionally displayed on the user interface. The indication text may read, for example: "Set respiration rate f, tidal volume VT and I:E ratio:" As soon as the user selects one of the operational controls (e.g., for setting the rate f), the device G, 10 changes into a data acceptance mode. In case of a correct operation of the operational control, the setting values are received by pressing the central operating knob (rotary knob). The data acceptance mode is ended and, with correct operation, the selection of the selection signal generator MSG, 33 of the respective rate setting element BE, 17 is also deactivated. The further operational controls to be operated (VT, I:E) can now, likewise highlighted, be selected. A new, adapted indication text H, 15 appears on the interface GUI, 13 (e.g., "set VT, I:E").

In the selection of the operational controls BE, 17, a distinction can be made between two modes of operation:
a parallel mode of operation; and
a sequential mode of operation.

In the parallel mode of operation, provisions are made that all the operational controls BE, 17 to be actuated one after the other are selected in parallel and at the same time. In the example mentioned above, all operational controls BE, 17 for setting the rate, for the tidal volume and for the inspiration-expiration ratio are also lit in parallel and thus selected at the same time. As soon as an operational control BE, 17 of the triple combination has been correctly operated, the selection is deactivated, such that the other two operational controls BE, 17 still to be operated remain selected. This process is carried out until all operational controls BE, 17 have been operated correctly. In the sequential mode of operation, a sequence can be preset and be selected by the user, in which the three (or more) operational controls (e.g., $BE_1$, $BE_2$, $BE_3$) BE, 17 are operated. Then, in each case only one operational control BE, 17 is visually selected, in particular the respective, next operational control to be operated. As soon as a correct operation of the respective operational control (e.g., $BE_1$) BE, 17 was detected, the selection is deactivated and the process is continued with the next operational control (e.g., $BE_2$) BE, 17 to be operated.

As soon as the user has to operate an operational control BE, 17, the device G, 10 changes into the data acceptance mode. The acceptance mode is—as already described above—ended by a correct operation of the user and the pressing of a central rotary knob operational control BE, 17. In this way, the user is guided by the necessary settings at the device G, 10 until all necessary respiration parameters (e.g., $FiO_2$—fraction of inspired oxygen, $P_{insp}$—inspiration pressure, Ti—inspiration time, f—respiration rate, PEEP—positive end expiratory pressure) for a selected respiration form have been set. The forms of a pressure-controlled respiration (e.g., PC-BiPAP, PC-CMV, PC-PSV), an assisted spontaneous breathing (e.g., SPN-CPAP/PS, SPN-PPS), as well as a volume-controlled respiration (e.g., VC-SIMV, VC-CMV) may be mentioned here as principal forms of respiration with a respirator. If all operating steps BS, 11 are executed, a correspondingly adapted indication text H, 15 (e.g., "respiration parameters are completely set") can be outputted on the interface GUI, 13. Optionally, the device G, 10 can carry out a checking of the set parameters for allowability. For this, allowable setting ranges for the respective respiration parameters in the respective mode of respiration are preconfigured in a memory, possibly differentiated by defined medical or clinical situations. The set ACTUAL parameter is compared with a SET value for allowability. As soon as a set ACTUAL parameter is not found within the range of allowability or differs from the SET value by a defined threshold value, the user can be informed via a corresponding message M, 21 (FIG. 3) on the graphical user interface GUI, 13. Consequently, it is possible that the device G, 10 returns automatically to the data acceptance mode to enable the user to set this parameter again. A context-sensitive checking of parameter values is thus made possible. An essential advantage can be seen in that the allowability ranges or the SET values can be modified at any time, such that the process is dynamically adapted to the respective state of scientific knowledge.

Basically, the monitor, on which the online help is displayed, must not be the same (or occupy the same display space) as the monitor, on which the visual indication H, 15 and/or the message M, 21 (FIG. 3) is displayed. Furthermore, at least one of the two above-mentioned monitors (for displaying the online help and/or for displaying the indication H, 15/message M, 21 (FIG. 3)) may also be retrieved onto a separate device (e.g., tablet device, Smartphone, laptop computer, etc.), whereby the external outputting device is in bidirectional data connection with the medical device G, 10. This has the advantage that the help information, which must be displayed according to the present invention (online help, visual indication H, 15, message M, 21 (FIG. 3)), does not mask essential outputs for the operation of the device G, 10 (as, for example, a graphic display of the $P_{aw}$—airway pressure and/or the graphical display of the flow over time).

As was already mentioned above, provisions are made in a preferred variant of the present invention for connecting an external device with a graphical user interface GUI, 13 to the medical device. The external device can be connected to device G, 10 via a wired or via a wireless network connection (e.g., WLAN, Bluetooth, etc.). In addition, the use is likewise possible via a transfer interface (e.g., router, WLAN-Accesspoint, etc.). It is also possible to provide a local area network (LAN) or wide area network (WAN), via which a plurality of external devices are connected to the medical device. Here, the user very comfortably accesses his local, especially mobile external device to operate the medical device. For this, the graphical interface GUI, 13 on the external device is used, as it were, as a "remote desktop" for the device G, 10. It is thus possible to display the online help, excerpts of the device operating file D, 31, the visual indication H, 15 and/or the message M, 21 (FIG. 3) on the external device.

The device control according to the present invention is explained in detail below with reference to FIG. 3 in an example, wherein indication texts H, 15 are likewise displayed on a graphical user interface GUI, 13 on the respirator. FIG. 3 comprises three views of a screen excerpt in different states. In the topmost view is shown an information box H, 15 (FIG. 2), which appears on the interface GUI, 13 as a window and which usually overlays displayed windows with the pressure and flow curves. Indication text H, 15 refers in this case to the next pending operation of the operational control BE, 17 for the I:E ratio. For this an excerpt from the online help may optionally be displayed on the monitor GUI, 13. In this example, the I:E respiration parameter is the third parameter of the three parameters to be operated (respiration rate f and tidal volume Vt) (which have already been set in this example). In the middle view, it is obvious that the respective operational controls BE, 17 are selected (rotary knob for I:E ratio and input confirmation via the central rotary knob, on the outside on the left and right). This is represented in FIG. 3 by the respective, selected operational controls BE, 17 being identified as luminous by beams pointing outwards, while other operational controls BE, 17 are not selected. Thus, the user's attention is drawn to which operational controls BE, 17 the user must operate or which parameter the user must set. After the user has set the rotary knob for inputting the I:E ratio and has confirmed the data input via the central entry knob (rotary knob), the activation signal AS, 27 (FIG. 2) is transmitted to the control module SM, 19 (FIG. 2). Consequently, the system determines that all respiration parameters have been inputted correctly and completely. Optionally, the control module SM, 19 (FIG. 2) can prompt a message M, 21 on the graphical user interface GUI, 13, as this is identified by way of example in this FIG. 3 in the lowermost view ("BiPAP parameters are set").

In conclusion, it should be pointed out that the description of the present invention and exemplary embodiments are basically defined as nonlimiting with regard to a defined physical embodiment of the present invention. It is especially obvious for a personal skilled in the art that the present invention can be embodied as divided partly or entirely in software and/or hardware and/or on a plurality of physical products—here in particular also computer program products.

While specific embodiments of the invention have been shown and described in detail to illustrate the application of the principles of the invention, it will be understood that the invention may be embodied otherwise without departing from such principles.

APPENDIX

| LIST OF REFERENCE NUMBERS | | |
|---|---|---|
| 10 | G | Device, anesthesia device or respirator |
| 11 | BS | Operating step |
| 13 | GUI | Graphical user interface |
| 15 | H | Indication, visual indication, information box, indicator arrow |
| 17 | BE | Operational control |
| 19 | SM | Control module |
| 21 | M | Message |
| 23 | MS | Selection signal |
| 25 | RS | Request signal |
| 27 | AS | Activation signal |
| 29 | ASG | Activation signal generator |
| 31 | D | Device operating file |
| 33 | MSG | Selection signal generator |
| 100 | Start S0 | Start-up |
| 110-109 | S1-S9 | Sequence of steps of the control process |
| 191 | CPU | Processor unit |
| 193 | MEM | Device memory |
| 195 | RAM | Additional memory, working memory |
| 197 | Z | Status detection unit |

What is claimed is:

1. A control module for a gas analyzer, a respirator or an anesthesia device for the guided execution of a sequence of operating steps, which require at least partially actuation of operational controls, and wherein the gas analyzer, respirator or anesthesia device comprises a plurality of operational controls comprising:

at least one selection signal generator receiving at least one request signal from the control module and consequently outputting at least one selection signal; and at least one activation signal generator generating at least one activation signal in the case of a correct operation of the operational control and for sending the activation signal to the control module and wherein the control module comprises:

at least one I/O interface with a graphical user interface on which at least one visual indication of the respective position of the operational control to be operated is outputted, whereby the visual indication comprises a direction indicator, which indicates the respective position of the operational control to be operated relative to the position of the visual indication on the graphical user interface, said graphical user interface comprising a touch screen, said touch screen comprising an input element, said direction indicator being oriented in a direction of one of said input element and an element outside of said touch screen; and a device memory, in which a device operating file is stored, the device operating file comprising at least one sequence of operating steps and means for reading out the sequence of operating steps.

2. A control module in accordance with claim 1, further comprising a status detection unit continuously detecting a device status of the gas analyzer, respirator or anesthesia device during the operation of the device and which, in case of an absent and/or incorrect operation of an operational control, outputs a context-sensitive message and/or the respectively generated visual indication with the dynamically adapted direction indicator on the graphical user interface.

3. A gas analyzer, respirator or anesthesia device, comprising:

a graphical user interface;

a plurality of operational controls for operating the respirator or the gas analyzer, respirator or anesthesia device the plurality of operational controls comprising:

at least one selection signal generator receiving at least one request signal from the control module consequently outputting at least one selection signal;

at least one activation signal generator generating at least one activation signal in the case of a correct operation of the operational control; and a control module receiving the activation signal from the activation signal generator and controlling the respirator or gas analyzer, respirator or anesthesia device within the framework of executing a sequence of operating steps, wherein the control module comprises:

at least one I/O interface with a graphical user interface on which at least one visual indication of the respective position of the operational control to be operated is outputted, whereby the visual indication comprises a direction indicator, which indicates the respective position of the operational control to be operated relative to the position of the visual indication on the graphical user interface, said graphical user interface comprising a touch screen, said touch screen comprising an input element, said direction indicator being oriented in a direction of one of said input element and an element outside of said touch screen; and a device memory, in which a device operating file is stored, the device operating file comprising at least one sequence of operating steps and means for reading out the sequence of operating steps.

4. A process for controlling a gas analyzer, respirator or anesthesia device when executing a sequence of operating steps, which require at least partially an actuation of operational controls, with access to a device memory, in which a device operating file is stored, comprising at least one sequence of operating steps and reading out of the sequence of operating steps, wherein for each read-out operating step of the sequence of operating steps for controlling the gas analyzer, respirator or anesthesia device, a sequence of operational controls, which must be operated for the respective operating step, is automatically detected, and wherein the following process steps are iteratively executed for each operational control of the detected sequence:

sending at least one request signal to a selection signal generator of the respective operational control;

outputting the selection signal to the respective operational control and/or outputting a visual indication with a direction indicator for position indication of the respective operational control to be operated relative to the position of the visual indication on the graphical user interface, said graphical user interface comprising a touch screen, said touch screen comprising an input element, said direction indicator being oriented in a direction of one of said input element and an element outside of said touch screen;

receiving at least one activation signal by an activation signal sensor, which is associated with the respective operational control, in case the respective operational control has been operated correctly; and iteratively executing the send-output-receive steps for the respective next operational control of the detected sequence.

5. A process in accordance with claim 4, further comprising:

providing the gas analyzer, respirator or anesthesia device with a graphical user interface, wherein the visual indication is outputted on the graphical user interface of the gas analyzer, respirator or anesthesia device, whereby the visual indication may comprise a context-sensitive message, which signals an absent and/or incorrect operation of the operational control.

6. A process in accordance with claim 5, wherein the visual indication, the direction indicator and/or a context-sensitive message is dynamically adapted to the position of the respective, next operational control to be operated.

7. A process in accordance with claim 4, further comprising:

detecting a device status in a context-sensitive manner; and displaying an excerpt of a device operating file on the graphical user interface depending on the device status detected.

8. A process in accordance with claim 4, wherein the selection signal and/or the visual indication are outputted directly on the operational control and on the graphical user interface, respectively, in case the operation of the operational control according to the detected sequence of operational controls is pending and/or in case of previous absent or incorrect operation of the operational control.

9. A process in accordance with claim 4, wherein the selection signal comprises a visual and/or acoustic signal.

10. A process in accordance with claim 4, wherein the selection signal is executed simultaneously with the displaying of a message and/or of the visual indication on the graphical user interface of the gas analyzer, respirator or anesthesia device.

11. A process in accordance with claim 4, wherein pairs of signals are formed by the request signal and respectively associated activation signal and wherein the thus formed pairs of signals and/or all visual indications are stored.

12. A process in accordance with claim 4, wherein a device operating file is indexed and comprises a plurality of entry points for the selection of the sequence of operating steps.

13. A process in accordance with claim 4, wherein a device operating file with the sequence of operating steps comprises electronic command sets for the operation and/or the maintenance of the gas analyzer, respirator or anesthesia device.

14. A control module for a gas analyzer, a respirator or an anesthesia device for the guided execution of a sequence of operating steps, which require at least partially actuation of operational controls, and wherein the gas analyzer, respirator or anesthesia device comprises a plurality of operational controls comprising:
  at least one selection signal generator receiving at least one request signal from the control module and consequently outputting at least one selection signal; and
  at least one activation signal generator generating at least one activation signal in the case of a correct operation of the operational control and for sending the activation signal to the control module and wherein the control module comprises:
  at least one I/O interface with a graphical user interface on which at least one visual indication of the respective position of the operational control to be operated is outputted, whereby the visual indication comprises a direction indicator, which indicates the respective position of the operational control to be operated relative to the position of the visual indication on the graphical user interface;
  a device memory, in which a device operating file is stored, the device operating file comprising at least one sequence of operating steps and means for reading out the sequence of operating steps; and
  a status detection unit continuously detecting a device status of the gas analyzer, respirator or anesthesia device during the operation of the device and which, in case of an absent and/or incorrect operation of an operational control, outputs a context-sensitive message and/or the respectively generated visual indication with the dynamically adapted direction indicator on the graphical user interface.

15. A process for controlling a gas analyzer, respirator or anesthesia device when executing a sequence of operating steps, which require at least partially an actuation of operational controls, with access to a device memory, in which a device operating file is stored, comprising at least one sequence of operating steps and reading out of the sequence of operating steps, wherein for each read-out operating step of the sequence of operating steps for controlling the gas analyzer, respirator or anesthesia device, a sequence of operational controls, which must be operated for the respective operating step, is automatically detected, and wherein the following process steps are iteratively executed for each operational control of the detected sequence:
  sending at least one request signal to a selection signal generator of the respective operational control;
  outputting the selection signal to the respective operational control and/or outputting a visual indication with a direction indicator for position indication of the respective operational control to be operated relative to the position of the visual indication on the graphical user interface;
  receiving at least one activation signal by an activation signal sensor, which is associated with the respective operational control, in case the respective operational control has been operated correctly;
  iteratively executing the send-output-receive steps for the respective next operational control of the detected sequence; and
  providing the gas analyzer, respirator or anesthesia device with a graphical user interface, wherein the visual indication is outputted on the graphical user interface of the gas analyzer, respirator or anesthesia device, whereby the visual indication may comprise a context-sensitive message, which signals an absent and/or incorrect operation of the operational control.

16. A process for controlling a gas analyzer, respirator or anesthesia device when executing a sequence of operating steps, which require at least partially an actuation of operational controls, with access to a device memory, in which a device operating file is stored, comprising at least one sequence of operating steps and reading out of the sequence of operating steps, wherein for each read-out operating step of the sequence of operating steps for controlling the gas analyzer, respirator or anesthesia device, a sequence of operational controls, which must be operated for the respective operating step, is automatically detected, and wherein the following process steps are iteratively executed for each operational control of the detected sequence:
  sending at least one request signal to a selection signal generator of the respective operational control;
  outputting the selection signal to the respective operational control and/or outputting a visual indication with a direction indicator for position indication of the respective operational control to be operated relative to the position of the visual indication on the graphical user interface;
  receiving at least one activation signal by an activation signal sensor, which is associated with the respective operational control, in case the respective operational control has been operated correctly; and
  iteratively executing the send-output-receive steps for the respective next operational control of the detected sequence, wherein the selection signal and/or the visual indication are outputted directly on the operational control and on the graphical user interface, respectively, in case the operation of the operational control according to the detected sequence of operational controls is pending and/or in case of previous absent or incorrect operation of the operational control.

* * * * *